United States Patent [19]

Strangio

[11] 4,036,900
[45] July 19, 1977

[54] MOLTEN SALT LIFT GAS SYSTEM FOR PRODUCTION OF CHLORINATED HYDROCARBONS

[75] Inventor: Vincent A. Strangio, Glenridge, N.J.
[73] Assignee: The Lummus Company, Bloomfield, N.J.
[21] Appl. No.: 610,061
[22] Filed: Sept. 3, 1975
[51] Int. Cl.$^2$ .................. C07C 17/10; C07C 17/15
[52] U.S. Cl. .................. 260/659 R; 260/656 R; 260/659 A; 260/660; 260/664
[58] Field of Search .......... 260/656 R, 659 R, 659 A, 260/660

[56] References Cited

U.S. PATENT DOCUMENTS

| | | | |
|---|---|---|---|
| 3,865,886 | 2/1975 | Schindler et al. | 260/659 R X |
| 3,879,480 | 4/1975 | Riegel et al. | 260/656 R |
| 3,917,727 | 11/1975 | Tsao | 260/660 X |
| 3,939,209 | 2/1976 | Sze et al. | 260/659 A X |
| 3,949,010 | 4/1976 | Sze | 260/659 A X |

FOREIGN PATENT DOCUMENTS 711,287  6/1965  Canada .................. 260/659 R

*Primary Examiner*—Daniel E. Wyman
*Assistant Examiner*—Thomas A. Waltz
*Attorney, Agent, or Firm*—Marn & Jangarathis

[57] ABSTRACT

Process for producing a chlorinated hydrocarbon by the use of molten salts containing a multivalent metal chloride in its higher and lower valence states by oxidation of the molten salt in an oxidation reactor and use of the oxidized salt in an oxychlorination/chlorination reactor for production of chlorinated hydrocarbons wherein gaseous effluent withdrawn from the oxidation reactor is employed as lift gas for lifting the molten salts for introduction into the upper portions of the oxidation reactor and oxychlorination/chlorination reactor, with the work being provided by expansion of the oxidizer effluent. In this manner, the need for a lift gas compressor is eliminated.

6 Claims, 3 Drawing Figures

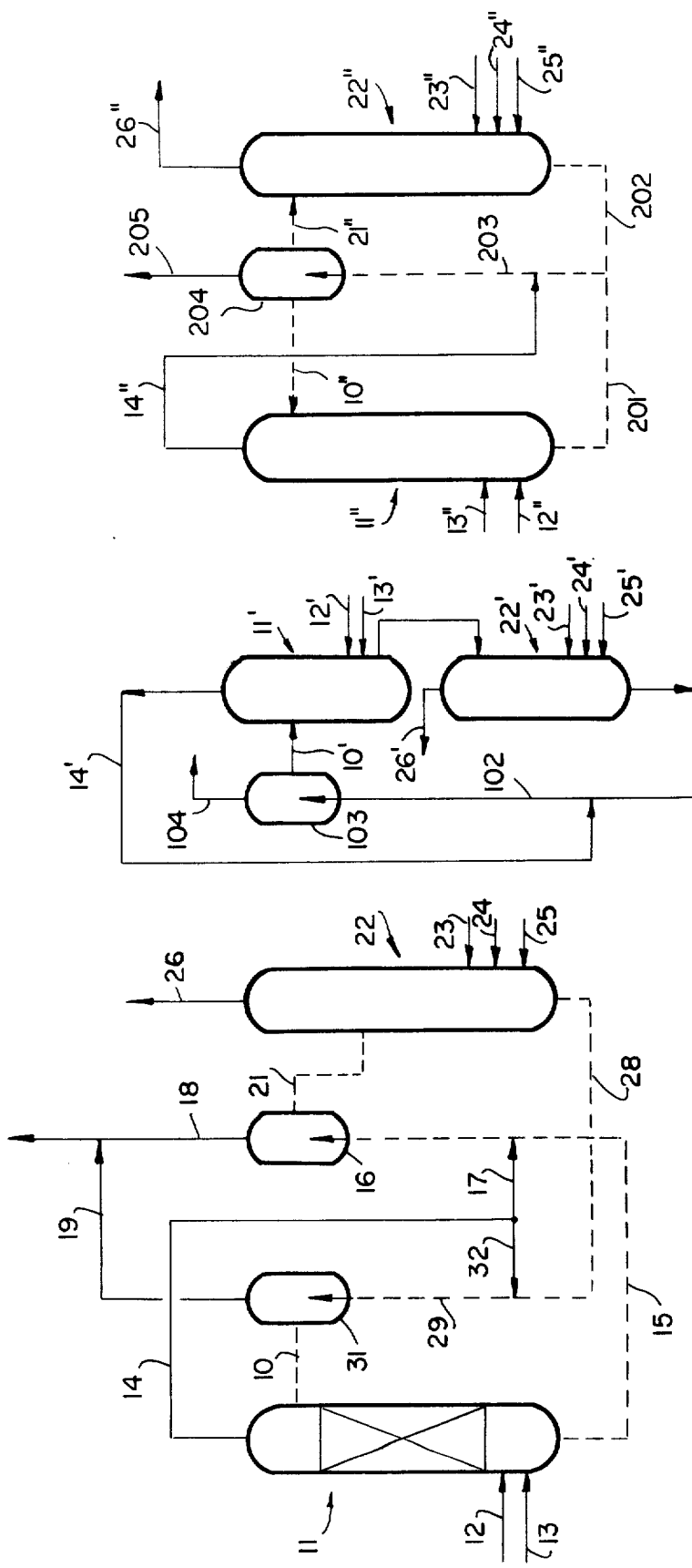

MOLTEN SALT LIFT GAS SYSTEM FOR PRODUCTION OF CHLORINATED HYDROCARBONS

This invention relates to the production of chlorinated hydrocarbons by the use of molten salts, and more particularly to a new and improved lift gas system for introducing the molten salt into the reactors of a chlorinated hydrocarbon production system.

In producing chlorinated hydrocarbons by molten salts, in general, the process involves the use of two reactors, with the molten salt being withdrawn from one of the reactors and introduced into the top of the other reactor, and visa versa. In general, the molten salt which is withdrawn from one reactor for introduction into the other reactor is withdrawn from the bottom of the reactor and lifted by a lift gas for introduction into the top of the other reactor. The use of a lift gas for effecting lifting of the molten salt requires a lift gas compressor, which increases the overall cost of the system.

Accordingly, an object of this invention is to provide for improved production of chlorinated hydrocarbons by use of molten salts.

Another object of the present invention is to provide an improved lift gas system and process for introducing molten salts into reactors for producing chlorinated hydrocarbons by the use of molten salts.

These and other objects of the present invention should become more apparent from reading the following detailed description thereof.

In accordance with the present invention, there is provided a process for producing a chlorinated hydrocarbon wherein a molten salt containing a multivalent metal chloride in its higher and lower valence state is contacted with an oxygen containing gas in an oxidation reactor to produce the oxychloride of the multivalent metal, with the molten salt withdrawn from the oxidation reactor being introduced into the upper portion of a chlorinated hydrocarbon production reactor wherein the molten salt is contacted with a hydrocarbon, to effect production of chlorinated hydrocarbon. The molten salt withdrawn from the lower portion of the chlorinated hydrocarbon production reactor is lifted by a lift gas for introduction into the upper portion of the oxidation reactor, with the lift gas being at least a portion of the gas stream recovered from the oxidation reactor. In effecting lifting of the molten salt, the lift gas is expanded from a first pressure to a second pressure, with the ratio of the first pressure to the second pressure being at least 1.5. In this manner, the work required for lifting the salt is provided by expansion of the gas withdrawn from the oxidation reactor, thereby eliminating the necessity for a separate lift gas compressor.

More particularly, the gas recovered from the oxidation reactor is at a first pressure and is expanded to a second pressure to effect lifting of the molten salt, with the ratio of the first pressure to second pressure being at least 1.5, preferably at least 1.8, and in general being no greater than 3.0, although as should be apparent values of greater than 3.0 could be employed. In general, the first gas pressure is in the order of from about 15 to 300 psia, preferably from 50 to 80 psia, and the second gas pressure is in the order of from about 5 to 200 psia, preferably from about 16 to 50 psia.

The oxidation reactor functions to enrich the oxychloride content of the molten salt and, accordingly, the oxygen is generally introduced into the oxidation reactor as air. As a result, the gaseous effluent withdrawn from the oxidation reactor is primarily comprised of nitrogen, and contains some amounts of unreacted oxygen. In most cases, the oxidation reactor is also employed to recover the chlorine values from a combustion gas produced from the combustion of chlorinated hydrocarbon by-products. The combustion gas which is also introduced into the oxidation reactor contains hydrogen chloride and/or chlorine, as well as unreacted oxygen, nitrogen and carbon oxide (carbon dioxide and/or carbon monoxide). The chlorine values are recovered by increasing the higher valent chloride content of the salt mixture. As a result, the gas withdrawn from the oxidation reactor, in such cases, includes, in addition to nitrogen and oxygen, carbon oxide, and minor amounts of hydrogen chloride and chlorine. All or a portion of the gas withdrawn from the oxidizer, as required, may be employed as a lift gas.

The oxidation reactor is generally operated at a temperature from about 600° F to 1000° F, and preferably at a temperature from about 700° F to about 950° F. The residence time is generally in the order from about 1 to about 100 seconds. The pressure of the oxidation reactor generally is in the order of from about 1 to about 20 atm.

The molten salt produced in the oxidation reactor is then passed to a chlorinated hydrocarbon production reactor. In the case where the oxidation reactor and chlorinated hydrocarbon production reactor are employed as stacked reactors, the molten salt flows, by gravity, to the chlorinated hydrocarbon production reactor. In the case where the oxidation reactor and chlorinated hydrocarbon production reactor are not employed as stacked reactors, the molten salt withdrawn from the oxidation reactor, is lifted to the top of the chlorinated hydrocarbon production reactor by the use of a lift gas, wherein the lift gas is the gas withdrawn from the oxidation reactor. As hereinabove described, the lift gas is expanded during lifting of the molten salt to the top of the chlorinated hydrocarbon production reactor.

The chlorinated hydrocarbon production reactor is generally operated at a temperature from about 600° F to about 1000° F, with the exact temperature being dependent upon the feed to the reactor. In general, the residence time is in the order of about 1 to about 100 seconds, but as should be apparent to those skilled in the art, shorter or longer residence times could be employed. In general, the pressure is in the order of from about 1 to about 20 atmospheres.

The feed to the chlorinated hydrocarbon production reactor may be either a hydrocarbon or partially chlorinated hydrocarbon, and as representative examples of such feeds, there may be mentioned: aromatic hydrocarbons, such as benzene; aliphatic hydrocarbons (saturated and/or olefinically unsaturated), preferably a $C_1$ to $C_4$ hydrocarbon; or a partially chlorinated derivative of such aromatic and aliphatic hydrocarbons. The most preferred feeds are ethane, ethylene, methane and partially chlorinated $C_1$ and $C_2$ hydrocarbons.

The present invention is particularly applicable to the production of chlorinated methanes from methane. In the production of chlorinated methanes, the oxychlorination/chlorination reactor is generally operated at a temperature of from about 700° F to about 950° F, and preferably at a temperature from about 800° F to about 860° F. The feed to the oxychlorination/chlorination reactor generally includes, in addition to fresh feed methane and hydrogen chloride and/or chlorine, recycle chlorinated methane(s), which are potentially convertible to the desired chlorinated methane product. A representative process for the production of chlorinated methanes is described in Application Ser. No. 299,114, filed on Oct. 19, 1972, and U.S. Application Ser. No. 299,848, filed on Oct. 24, 1972, now abandoned.

The present invention also has a particular applicability to the production of vinyl chloride from ethane and/or ethylene, with the oxychlorination/chlorination reactor being operated at a temperature from about 700° F to about 1000° F, preferably a temperature from about 750° F to about 950° F. The feed to the oxychlorination/chlorination reactor generally also includes recycled components in particular, ethyl chloride, ethylene and unreacted ethane in the case where ethane is used as fresh feed.

The 1,2-dichloroethane produced in the oxychlorination/chlorination reactor is dehydrochlorinated to vinyl chloride. The dehydrochlorination can be effected by conventional thermal or catalytic procedures. Alternatively, and preferably, the dehydrochlorination is effected by direct contact with a molten salt containing the higher and lower valent forms of the multivalent metal chloride and also the oxychloride. In such a case, the oxychlorination/chlorination reactor is preferably divided into two vertical reaction sections, with molten salt, which is lifted by the lift gas system, being introduced into the top of both sections of the single reactor.

The molten salt mixture, as hereinabove described, contains a chloride of a multivalent metal; that is a metal having more than one positive valence state, such as manganese, iron, copper, cobalt and chromium, preferably copper. The molten salt mixture also generally includes a metal salt melting point depressant which is nonvolatile and resistant to the action of oxygen at the process conditions, such as an alkali metal chloride; in particular, potassium and lithium chloride, or a heavy metal chloride; i.e., heavier than copper, of Groups I, II, III and IV of the Periodic Table. A preferred molten salt mixture contains copper chlorides and potassium chlorides, with the potassium chloride generally being present in an amount from about 20% to about 40%, by weight.

The invention will be described with respect to the following drawings, wherein:

FIG. 1 is a simplified schematic flow diagram of an embodiment of the present invention.

FIG. 2 is a simplified schematic flow diagram of a further embodiment of the present invention; and FIG. 3 is a simplified schematic flow diagram of still another embodiment of the present invention.

Referring now to FIG. 1, a molten salt, containing a multivalent metal chloride in its higher and lower valence state, such as a salt containing cupric and cuprous chloride, and potassium chloride, as a melting point depressant, in line 10 is introduced into the top of an oxidation reactor 11, maintained at a pressure from about 1 to about 20 atm. A compressed oxygen containing gas, such as air, in line 12, and a by-product combustion effluent, in line 13, comprising chlorine and/or hydrogen chloride, as well as carbon oxide, water vapor, nitrogen and perhaps unreacted oxygen are introduced into reactor 11. The by-product combustion effluent is generally produced by the combustion of chlorinated hydrocarbon by-products which are not marketable and/or suitable for recycle to the chlorinated hydrocarbon production zone. As a result of the countercurrent contact between the feeds introduced through lines 12 and 13 and the descending molten salt mixture, the salt is oxidized to produce copper oxychloride, and the hydrogen chloride and/or chlorine introduced with the combustion effluent are absorbed by the molten salt to produce cupric chloride.

An effluent gas, including water vapor, nitrogen, carbon oxide, unabsorbed hydrogen chloride, and perhaps chlorine and unreacted oxygen is withdrawn from the top of reactor 11 through line 14, the gas being at a pressure from about 1 to about 20 atm.

Molten salt is withdrawn from the bottom of reactor 11 through line 15 and is lifted into a lift gas separator 16 by a lift gas comprised of a portion of the effluent in line 14 and provided through line 17. The separator 16 is at a pressure from about 5 to about 200 psia to provide a ratio of pressure in line 17 to pressure in separator 16 of at least 1.5, whereby the work required for lifting the molten salt through the lift pipe is provided by the expansion of the lift gas into the separator 16.

The lift gas withdrawn from separator 16, through line 18, is combined with additional lift gas in line 19 and further processed, as required.

Molten salt withdrawn from separator 16 through line 21 is introduced into the upper portion of the chlorinated hydrocarbon production reactor 22. The molten salt introduced into reactor 22 is countercurrently contacted with hydrogen chloride and/or chlorine introduced through line 23, fresh hydrocarbon and/or chlorinated hydrocarbon introduced through line 24 and recycle components, if any, introduced through line 25. As a result of the countercurrent contact, the hydrocarbon and/or chlorinated hydrocarbon, introduced as fresh feed and/or recycle, are oxychlorinated/chlorinated to produce chlorinated hydrocarbons, with the oxychloride content of the melt being depleted as a result of the oxychlorination reaction. The hydrocarbon effluent is withdrawn from reactor 22 through line 26 for further processing, as known in the art.

Molten salt withdrawn from the bottom of reactor 22 through line 28 is lifted through a gas lift pipe 29 into a gas lift separator by a lift gas provided through line 31, which is another portion of the effluent withdrawn from oxidation reactor 11 through line 14. As hereinabove described with respect to lifting of molten salt into separator 16, the work required for lifting of the molten salt into separator 31 is provided by expanding the lift gas into the separator 31 which is operated at a pressure from about 5 to about 200 psia to provide a ratio of pressure in line 31 to pressure in separator 31 of at least 1.5.

The separated lift gas is withdrawn through line 19 and combined with the lift gas in line 18 for further processing, as required. The molten salt recovered in separator 31 is introduced into the top of the oxidation reactor 11 through line 10, as hereinabove described.

As should be apparent from the above description, the molten salt required for introduction into the oxidation reactor 11 and the chlorinated hydrocarbon production reactor 22 is introduced by means of a lift gas, and without the necessity of employing a separate lift gas compressor.

Referring to FIG. 2, which illustrates a further embodiment of the present invention, wherein the oxidation reactor and chlorinated hydrocarbon production reactor are employed as stacked reactors. In this embodiment, like features are designated by prime numerals.

As described with reference to FIG. 1, molten salt in line 10' is introduced into an oxidation reactor 11' wherein the molten salt is countercurrently contacted with oxygen introduced through line 12' and a chlorinated hydrocarbon combustion effluent introduced through line 13'. An effluent gas is withdrawn from the oxidation reactor 11' through line 14'.

Molten salt withdrawn from reactor 11', flows by gravity, into the chlorinated hydrocarbon production reactor 22' wherein the molten salt is countercurrently contacted with chlorine and/or hydrogen chloride introduced through line 23', fresh hydrocarbon feed introduced through line 24' and recycle components, if any, introduced through line 25'. A chlorinated hydrocarbon effluent is withdrawn from reactor 22' for further processing, through line 26'.

Molten salt is withdrawn from reactor 22' through line 101 and lifted through gas lift pipe 102 into a gas lift separator 103 by a lift gas, comprised of the effluent gas in line 14'. As should be apparent, if required, only a portion of the effluent gas in line 14' may be used for lifting the molten salt through lift gas pipe 102. As hereinabove described, the work required for lifting the molten salt into separator 103 is provided by expanding the lift gas into separator 103.

The lift gas separated in separator 103 is withdrawn through line 104 for further processing, as required.

Molten salt withdrawn from separator 103 is introduced into oxidation reactor 11' through line 10', as hereinabove described.

Still another embodiment of the invention is illustrated in FIG. 3 wherein like parts are designated by like double prime numerals.

Referring to FIG. 3, molten salt in line 10'' is introduced into the top portion of an oxidation reactor 11'' wherein the molten salt is countercurrently contacted with an oxygen containing gas introduced through line 12'' and a combustion effluent introduced through line 13''. An effluent gas is withdrawn from oxidation reactor 11'' through line 14''.

Molten salt withdrawn from oxidation reactor 11'', through line 201, is combined with molten salt withdrawn from chlorinated hydrocarbon production reactor 22'' through line 202. The combined molten salt is lifted through gas lift pipe 203 into a gas lift separator 204 by a lift gas comprised of the effluent gas in line 14''. As hereinabove described, the work required for lifting salt is provided by expansion of the gas in line 14'' into the separator 204.

The separated lift gas is withdrawn from separator 204 through line 205 for further processing, as required.

A first portion of the molten salt is withdrawn from separator 204 through line 10'' for introduction into the oxidation reactor 11''.

A second portion of the molten salt is withdrawn from separator 204 through line 21'' and introduced into the upper portion of the chlorinated hydrocarbon production reactor 22'' wherein the molten salt is contacted with fresh hydrocarbon feed in line 24'', hydrogen chloride and/or chlorine in line 23'' and recycle components, if any, in line 25''. A chlorinated hydrocarbon effluent is withdrawn from reactor 22'' through line 26''.

As should be apparent, from the description of the hereinabove described embodiments, molten salt can be lifted into one or more reactors of a chlorinated hydrocarbon production system, employing molten salts, by use of the effluent withdrawn from the oxidation reactor, as a lift gas, without the necessity of employing a separate lift gas compressor.

The hereinabove described embodiments may be modified within the spirit and scope of the present invention. Thus, for example, a combustion effluent need not be introduced into the oxidation reactor. As a further modification, an aqueous hydrogen chloride solution may also be introduced into the oxidation reactor.

As still another modification, the gas recovered from the oxidation vessel may be subjected to other processing steps or procedures prior to utilization thereof as a lift gas, instead of effecting direct use thereof as disclosed.

Numerous modifications and variations of the present invention are possible within the above teachings and, therefore, within the scope of the appended claims, the invention may be practiced otherwise than as particularly described.

What is claimed is:

1. In a process for producing a chlorinated hydrocarbon wherein a molten salt containing a multivalent metal chloride in its higher and lower valence state is contacted with an oxygen containing gas in an oxidation reaction zone to produce the oxychloride of the multivalent metal, molten salt withdrawn from the oxidation reaction zone being introduced into a chlorinated hydrocarbon production zone wherein molten salt is contacted with a hydrocarbon to produce chlorinated hydrocarbon and molten salt withdrawn from the chlorinated hydrocarbon production zone is introduced into the oxidation reaction zone, the improvement comprising:

withdrawing a gas stream from the oxidation reaction zone;

directly employing, without compression, a portion of the gas stream withdrawn from the oxidation reaction zone at an initial pressure corresponding to the pressure prevailing in the oxidation reaction zone to lift molten salt withdrawn from the chlorinated hydrocarbon production zone to an elevated height for introduction into an upper portion of the oxidation reaction zone by expansion of said portion of the gas stream from said initial pressure to an expanded pressure to provide a ratio of said initial pressure to said expanded pressure of said portion of the gas stream of at least 1.5; and employing, without compression, another portion of the gas stream withdrawn from the oxidation reaction zone at an initial pressure corresponding to the pressure prevailing in the oxidation reaction zone for lifting molten salt withdrawn from the oxidation reaction zone to an elevated height for introduction into an upper portion of the chlorinated hydrocarbon production zone by expansion of said another portion of the gas stream from said initial pressure to an expanded pressure to provide an initial pressure to expanded pressure ratio of at least 1.5.

2. The process of claim 1 wherein said portion of the gas stream withdrawn from the oxidation reaction zone is employed for lifting molten salt withdrawn from the chlorinated hydrocarbon production zone into a first molten salt separation zone wherein molten salt is separated from the gas and introduced into the oxidation reaction zone and said another portion of the gas stream withdrawn from the oxidation reaction zone is employed for lifting molten salt withdrawn from the oxidation reaction zone into a second molten salt separation zone wherein molten salt is separated from the gas and introduced into the chlorinated hydrocarbon production zone.

3. The process of claim 1 wherein the molten salt withdrawn from the oxidation reaction zone and the chlorinated hydrocarbon production zone are combined and lifted by the gas stream into a molten salt separation zone, a first portion of the molten salt being withdrawn from the separation zone and introduced into the oxidation reaction zone and a second portion of the molten salt being withdrawn from the separation zone and introduced into the chlorinated hydrocarbon production zone.

4. The process of claim 1 wherein the initial pressure is from about 15 to about 300 psia and the expanded pressure is from about 5 to about 200 psia.

5. The process of claim 4 wherein the pressure ratio is at least 1.8.

6. The process of claim 5 wherein the initial pressure is from about 50 to about 80 psia and the expanded pressure is from about 16 to about 50 psia.

* * * * *